United States Patent [19]

Enz

[11] Patent Number: 5,602,176

[45] Date of Patent: Feb. 11, 1997

[54] PHENYL CARBAMATE

[75] Inventor: Albert Enz, Basel, Switzerland

[73] Assignee: Sandoz Ltd., Basel, Switzerland

[21] Appl. No.: 466,502

[22] Filed: Jun. 6, 1995

Related U.S. Application Data

[63] Continuation of Ser. No. 353,848, Dec. 24, 1994, abandoned, which is a continuation of Ser. No. 110,622, Aug. 23, 1993, abandoned, which is a continuation of Ser. No. 6,904, Jan. 21, 1993, abandoned, which is a continuation of Ser. No. 925,365, Aug. 4, 1992, abandoned, which is a continuation of Ser. No. 859,171, Mar. 27, 1992, abandoned, which is a continuation of Ser. No. 750,334, Aug. 27, 1991, abandoned, which is a continuation of Ser. No. 664,189, Mar. 4, 1991, abandoned, which is a continuation of Ser. No. 589,343, Sep. 27, 1990, abandoned, which is a continuation of Ser. No. 408,640, Sep. 18, 1989, abandoned, which is a continuation of Ser. No. 285,177, Dec. 15, 1988, abandoned, which is a continuation of Ser. No. 162,568, Mar. 1, 1988, abandoned.

[30] Foreign Application Priority Data

Mar. 4, 1987 [DE] Germany ............................ 37 06 914.4

[51] Int. Cl.$^6$ ........................................ A61K 31/27
[52] U.S. Cl. ............................... 514/490; 560/136
[58] Field of Search ............................ 560/136; 514/490

[56] References Cited

U.S. PATENT DOCUMENTS 4,469,700  9/1984  Somers ................................ 424/265

FOREIGN PATENT DOCUMENTS 193926  9/1986  European Pat. Off. .

*Primary Examiner*—Michael L. Shippen
*Attorney, Agent, or Firm*—Robert S. Honor; Melvyn M. Kassenoff; Thomas O. McGovern

[57] ABSTRACT

The (S)-N-ethyl-3-[(1-dimethylamino)ethyl]-N-methyl-phenylncarbamate in free base or acid addition salt form is useful as pharmaceutical, particularly for systemic transdermal administration.

12 Claims, No Drawings

PHENYL CARBAMATE

This is a continuation of application Ser. No. 08/353,848 filed Dec.12, 1994, which in turn is a continuation of application Ser. No. 08/110,622, filed Aug. 23, 1993, which in turn is a continuation of application Ser. No. 08/006,904, filed Jan. 21, 1993, which in turn is a continuation of application Ser. No. 07/925,365, filed Aug. 4, 1992, which in turn is a continuation of application Ser. No. 07/859,171, filed Mar. 27,1992, which in turn is a continuation of application Ser. No. 07/750,334, filed Aug. 27,1991, which in turn is a continuation of application Ser. No. 07/664,189, filed Mar. 4, 1991 which in turn is a continuation of application Ser. No. 07/589,343, filed Sep. 27, 1990, which in turn is a continuation of application Ser. No. 07/408,640, filed Sep. 18, 1989, which in turn is a continuation of application Ser. No. 07/285,177, filed Dec. 15, 1988, which in turn is a continuation of application Ser. No. 07/162,568, filed Mar. 1, 1988, all now abandoned.

The present invention relates to a novel phenyl carbamate with anticholinesterase activity.

More particularly the invention relates to the (S)-N-ethyl-3-[(1-dimethylamino)ethyl]-N-methyl-phenyl-carbamate of formula I

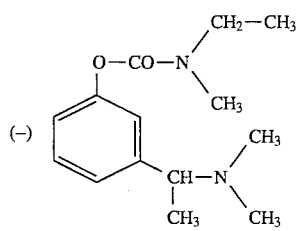

in free base or acid addition salt form.

As can be seen from this formula, in free base form the sign of rotation of the compound of formula I is (−). However in acid addition salt form it may be (+) or (−). For instance the sign of rotation of the hydrogen tartrate is (+). The present invention covers the free base form as well as the acid addition salt forms, independently of their sign of rotation.

The racemic mixture (±)-N-ethyl-3-[(1-dimethylamino)ethyl]-N-methyl-phenyl-carbamate in form of its hydrochloride is known from the European patent application 193,926 where it is identified as RA$_7$ HCl.

According to this disclosure the racemate in free base form is obtained by amidation of α-m-hydroxyphenylethyldimethylamine with a corresponding carbamoyl halogenide. The resulting compound and its pharmacologically acceptable acid addition salts, which can be prepared from the free base in known manner, are disclosed as acetylcholinesterase inhibitors in the central nervous system.

It has now surprisingly been found that the (−)-enantiomer of formula I and its pharmacologically acceptable acid addition salts, hereinafter referred to as compounds according to the invention, exhibit a particularly marked and selective inhibition of the acetylcholinesterase.

These findings are unexpected, particularly since it is not believed that the dialkylaminoalkyl side chain, which contains the optically active centre, is mainly responsible for the acetylcholinesterase inhibiting activity of the phenyl carbamates.

The compounds according to the invention have never been specifically disclosed in the literature. The free base may be prepared from the racemate by separation of the enantiomers in accordance with known methods, e.g. using di-0,0'-p-toluyl-taratric acid. The acid addition salts may be prepared from the free base in known manner. These include e.g. the hydrogen tartrate.

The compounds according to the invention exhibit pharmacological activity as indicated in standard tests and are therefore useful as pharmaceuticals. They reach the central nervous system rapidly after s.c., i.p. or p.o. administration in rats. They exert a brain region-selective inhibition of acetylcholinesterase activity, hippocampal and cortical enzyme being more inhibited than acetylcholinesterase originating from striatum and pons/medulla. Furthermore they have a long duration of action.

The following results, for example, illustrate the pharmacological profile of the compounds according to the invention as compared to the corresponding isomers and racemates. Compound A is the compound of formula I in form of its hydrogen tartrate. Compound B is the optical isomer of said salt. C designates the racemic mixture of the compound of formula I and its optical isomer, in form of the hydrochloride.

In Vitro Assays

Electrically evoked $^3$H-acetylcholine release from rat hippocampal slices

Electrically evoked $^3$H-acetylcholine ($^3$H-ACh) release from rat hippocampal slices is a functional in vitro model to investigate presynaptic muscarinic autoreceptor agonists and antagonists. This model can also be used as an indirect method to evaluate drugs which inhibit acetylcholinesterase (AChE). Inhibition of AChE activity leads to the accumulation of endogenous ACh which then interacts with presynaptic muscarinic autoreceptors and inhibits further release of $^3$H-ACh.

Rat hippocampal slices (Wistar strain, 180–200 g) are prepared by chopping into cross sections whole hippocampal slices at a distance of 0.3 mm with a McIlwain tissue chopper. Hippocampal slices obtained from 3 rats are incubated for 30 min. at 23° C. in 6 ml Krebs-Ringer containing 0.1 uCi $^3$H-choline and transferred into the superfusion chamber and superfused with Kreb's medium containing 10 μM hemicholinium-3 at a rate of 1.2 ml/min. at 30° C. Collection of 5 min. fractions of the superfusate begins after 60 min. of superfusion. Two periods of electrical stimulation (2 Hz rectangular pulses 2 msec, 10 mA, 2 min.) are applied after 70 min. ($S_1$) and after 125 min. ($S_2$) of superfusion. Test substances are added 30 min. before $S_2$ and are present in the superfusion medium until 145 min. of superfusion. At the end of the experiments the slices are solubilized in conc. formic acid and tritium content is determined in the superfusate and the solubilized slices. Tritium outflow is expressed as the fractional rate of tritium outflow per min. Electrically evoked tritium outflow is calculated by subtraction of the extrapolated basal tritium outflow from the total tritium outflow during the two min. of electrical stimulation and the following 13 min. and is expressed as percent of the tritium content at the beginning of the sample collection. Drug effects on stimulation evoked tritium outflow are expressed as the ratios $S_2/S_1$. All experiments are run in dublicates using a programmable 12 channel superfusion system. For the calculation a computer program is used.

In this test compound A inhibits electrically evoked $^3$H-ACh release from hippocampal slices by approximately 40% (100 μM) while racemate C (100 μM) inhibits by approximately 25%. The inhibitory effects of compound A and racemate C can be antagonized by atropine. These results are compatible with an AChE-inhibiting activity. Compound B is inactive in this model.

Acetylcholinesterase inhibition in different rat brain regions

AChE preparations of different rat brain regions (Cortex, hippocampus and striatum) are used in this test and the $IC_{50}$ (inhibitory concentrations in µM) are determined. The enzyme preparations are preincubated with the inhibitor 15 minutes before the determination.

The AChE activity is measured according to the method described by Ellman (Arch. Biochem. Biophys. 82, 70, 1959). Rat brain tissue is homogenized in cold phosphate buffer pH 7.3 (0.25 mM) containing 0.1% of Triton X-100. After centrifugation aliquots of the clear supernatant is used as enzyme source. The enzyme is preincubated with different concentrations of the inhibitor. After different times, substrate (acetylthiocholinjodide 0.5 mM) is added and the remaining activity determined.

The results are given in the following table 1:

TABLE 1

| $IC_{50}$ | Cortex | Hippocampus | Striatum |
|---|---|---|---|
| Compound A | 2.8 | 3.7 | 3.0 |
| Compound B | 16.1 | 14.5 | 13.8 |
| Racemate C | 3.2 | 3.9 | 3.2 |

As can be seen from this table the AChE inhibition with compound A is slightly superior than that with racemate C, whereas compound B is significantly less active.

Acetylcholinesterase inhibition ex vivo in different rat brain regions 30 minutes after administration of different doses of compound A, the AChE activity in different rat brain regions is measured ex vivo. The method is as disclosed above. The $IC_{50}$ values found are 7 µmol/kg p.o. in striatum, 4 µmol/kg p.o. in hippocampus and 2 µmol/kg p.o. in cortex. The $IC_{50}$ obtained after administration of the racemate C are for all examined regions about 2–3 times higher. Six hours after administration of compound A (10 µmol/kg p.o.) the AChE in striatum is still inhibited by 16%, whereas at the same time the activities in cortex and hippocampus are inhibited by 39% and 44% respectively.

In Vivo Assays

Influence on dopamine metabolism

Male OFA rats (150–200 g) were used both for acute and subchronic experiments. The animals are maintained under 12 hour periods of light and dark. The animals are sacrificed always between 11.00 and 13.00 h. The brains are excised immediately, dissected on ice according to the method of GLOWINSKI and IVERSEN, J. Neurochem. 13, 655 (1966), frozen on dry ice and the tissue samples stored at −80° C. until analysis.

Dopamine and its metabolites DOPAC (3,4-dihydroxyphenylacetic acid) and HVA (homovanillic acid) are determined in brain tissue extracts which are obtained by homogenisation of the stored brain tissue samples in 0.1N HCl containing 0.05 mM ascorbic acid and subsequent centrifugation. Striatal and cortical tissues are used.

The determination of the metabolites is performed using either the gas chromatography/mass fragmentography (GCMS) technique as described by KAROUM et al., J. Neurochem. 25, 653 (1975) and CATABENI et al., Science 178, 166 (1972) or the fluorometric method as described by WALDMEIER and MAITRE, Analyt. Biochem. 51, 474 (1973). For the GCMS method, tissue extracts are prepared by adding known amounts of deuterated monoamines and their respective metabolites as internal standards.

Dopamine metabolism in striatum is increased following the administration of compounds A and B and racemate C (This property is a consequence of the acetylcholine accumulation provoked by said compounds). However compound A is more active than compound B and racemate C in enhancing the striatal dopamine metabolite concentration.

Muscarinic and nicotinic effects on brain glucose utilisation

Changes in the functional activity of the CNS are associated with altered deoxyglucose (DOG) utilisation in the brain which can be visualised simultaneously in several brain regions using the autoradiographic method of Sokoloff et al., J. Neurochem. 28, 897 (1977). The administration of cholinergic drugs either direct (muscarinic agonists) or indirect (accumulation of acetylcholine) induces in this model a characteristic "fingerprint" pattern by modifying the regional glucose metabolism.

Male Wistar rats (150–200 g) are used. Drugs are administered at various doses and by different routes (i.v., p.o., i.p.) to animals. [14C]-2-deoxyglucose (125 µC/kg) is injected 45 min. before the animals are sacrificed. The brains are immediately excised, frozen at −80° C. and subsequently cut in slices with a thickness of 20 µm. The optical densities of the radiographic images are measured according to a modification of Sokoloff et al.

After p.o. application of compounds A and B (7.5 µmol/kg) significant changes in DOG utilisation in various rat brain regions are observed. The effect of compound A is more potent than that of compound B during the initial 30 minutes. The most marked changes are found in the visual regions and the anteroventral thalamus and also in the lateral habenula mucleus.

Acetylcholine levels in different rat brain regions

The effects of compounds A and B and racemate C as AChE inhibitors in vivo is determined by measuring the levels of ACh in different regions of rat brain at various times after drug administration.

OFA rats (200–230 g) are used. The animals are killed by microwave irradiation focused on the head (6 kW operating power 2450 Mhz exposure 1.7 sec., Pueschner Mikrowellen-Energietechnik, Bremen). The brains are removed dissected according to Glowinski and Iversen (1966) and stored at −70° C. until analysis. The brain parts are homogenized in 0.1M perchloric acid containing internal deuterated standards of ACh-$d_4$ and Ch(choline)-$d_4$. After centrifugation, endogenous ACh and Ch together with their deuterated variants are extracted with dipicrylamine (2,2',4,4',6,6'-hexanitrodiphenylamine) in dichlormethane as ion pairs. The Ch moieties are derivatized with propionyl chloride and the resulting mixture of ACh and propyl choline derivatives are demethylated with sodiumbenzenethiolate and analyzed by mass-fragmentography according to Jenden et al. Anal. Biochem., 55, 438–448, (1973).

A single application of 25 µmol/kg p.o. increases ACh concentrations in striatum, cortex and hippocampus. The maximal effect is achieved about 30 min. after oral application and declines during the next 3–4 hours. In cortex and hippocampus the ACh levels are still significantly higher at 4 hours compared to controls. The effects are dose dependent. The influence of compound B is significantly weaker than that induced by racemate C, and the influence of racemate C is significantly weaker than that induced by compound A.

Furthermore the compounds according to the invention are indicated to be well tolerated and orally active, and they have a long duration of action, e.g. in the above and other standard tests.

The compounds according to the invention are therefore useful for the treatment of senile dementia, Alzheimer's disease, Huntington's chorea, tardive dyskinesias, hyperkinesia, mania, acute confusion disorders, Down's syndrome and Friedrich's ataxia.

For these indications, the appropriate dosage will, of course, vary depending upon, for example, the compound according to the invention employed, the host, the mode of administration and the nature and severity of the condition being treated. However, in general, satisfactory results in animals are indicated to be obtained at daily dosages from about 0.01 to about 10 mg/kg, e.g. about 0.1 to about 5 mg/kg animal body weight. In larger mammals, for example humans, an indicated daily dosage is in the range from about 0.1 to about 25 mg, e.g. about 0.1 to about 5 mg of a compound according to the invention, conveniently administered, for example, in divided doses up to four times a day.

The compounds according to the invention may be administered by any conventional route, in particular enterally, preferably orally, e.g. in the form of tablets or capsules, or parenterally, e.g. in the form of injectable solutions or suspensions.

The above mentioned compound A is the preferred compound for the above mentioned indications. The preferred indication is senile dementia.

The present invention also provides pharmaceutical compositions comprising a compound according to the invention in association with at least one pharmaceutical carrier or diluent. Such compositions may be manufactured in conventional manner. Unit dosage forms contain, for example, from about 0.025 to about 12.5 mg of a compound according to the invention. Conveniently an acid addition salt form is used. The preferred salt form is compound A, especially for orally administrable forms, e.g. from the point of view of stability.

In the following example, the temperatures are uncorrected and are in degrees centigrade.

EXAMPLE 1

(S)-N-ethyl-3-[(1-dimethylamino)ethyl]-N-methyl-phenyl-carbamate 130 g of (±)-N-ethyl-3-[(1-dimethylamino)ethyl]-N-methyl-phenylcarbamate and 210 g of (+)-di-0,0'-p-toluoyl tartaric acid monohydrate are dissolved while heating in 1.3 liter of methanol/water (2:1). The salt precipitated after cooling is filtered and recrystallised 3 times from methanol/water (2:1). The (S)-enantiomer is released by partitioning between 1N NaOH and ether. $[\alpha]_D^{20} = -32.1°$ (c=5 in ethanol).

The hydrogen tartrate of the title compound (from ethanol) melts at 123°–125°. $[\alpha]_D^{20} = +4.7°$ (c=5 in ethanol).

The present invention furthermore provides the systemic transdermal application of the phenyl carbamates of formula I',

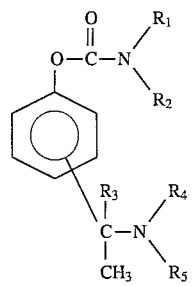

wherein $R_1$ is hydrogen, lower alkyl, cyclohexyl, allyl or benzyl, $R_2$ is hydrogen, methyl, ethyl or propyl, or $R_1$ and $R_2$ together with the nitrogen to which they are attached form a morpholino or piperidino radical, $R_3$ is hydrogen or lower alkyl, $R_4$ and $R_5$ are the same or different and each is a lower alkyl, and the dialkylaminoalkyl group is in the meta, ortho or para position, in free base or pharmaceutically acceptable acid addition salt form.

The compounds of formula I' and their pharmaceutically acceptable acid addition salts as well as their preparation and their use as acetylcholinesterase inhibitors are known from the above mentioned European patent application 193,926.

The compounds of formula I' include for example the above defined compound A and racemate C.

It has now surprisingly been found that the compounds of formula I' in free base or pharmaceutically acceptable acid addition salt form, hereinafter referred to as compounds for administration according to the invention, exhibit unexpectedly good skin penetration when administered percutaneously.

The penetration through the skin of the compounds for administration according to the invention may be observed in standard in vitro or in vivo tests.

One in vitro test is the well known diffusion test which may be effected according to the principles set out in GB 2098865 A and by T. J. Franz in J. Invest. Dermatol. (1975) 64, 194–195. Solutions containing the active agent in unlabelled or radioactively labelled form are applied to one side of isolated pieces of intact human skin or hairless rat skin about 2 cm² in area. The other side of the skin is in contact with physiological saline. The amount of active agent in the saline is measured in conventional manner, e.g. by HPLC or spectrophotometric techniques, or by determining the radioactivity.

In this test using rat skin the following penetration rates, for example, have been found:

Above defined compound A: 23.6±14.9%

Compound of formula I in free base form: 28.0±8.2%

Moreover it has been found that transdermal administration of the compounds for administration according to the invention induces a long-lasting and constant inhibition of acetylcholinesterase activity as indicated in standard tests, with a slow onset of action, which is particularly advantageous with respect to the tolerability of these compounds.

For example the acetylcholinesterase inhibition in different rat brain regions ex vivo has been measured after transdermal administration of the compounds for administration according to the invention, and compared to the inhibition obtained after administration via different routes.

The compounds are dissolved in or diluted with n-heptane to a concentration of 1 or 3 mg/20 μl. Male rats (OFA strain, ca. 250 g) are shaved in the neck region and the solution is applied with a micropipette on the skin. The application place is immediately covered using a thin plastic film and a plaster. The animal has no access to the plaster. Various times after the administration the animals are killed by decapitation and the remaining AChE activity is measured.

Transdermal administration of the above defined compound A, for example, induces a long-lasting, dose-dependent inhibition of AChE activity. In contrast to the rapid onset of the effect after either oral or subcutaneous application (max. 15 and 30 min. respectively), the AChE inhibition occurs slowly after this application route (max.>2 hours) without affecting the brain region selective AChE inhibition.

The results are shown in the following table 2. Twenty four hours after transdermal application, the AChE activity is still inhibited in central and peripheral regions. After the same time, orally applied compound A has no effect on the enzyme, whereas after the s.c. application only the enzyme in the heart is significantly inhibited.

intravenous administration. The amount of pharmaceutically active agent to be administered will individually depend on the drug release characteristics of the pharmaceutical compositions, the drug penetration rate observed in in vitro and in vivo tests, the potency of active agent, the size of the skin contact area, the part of the body to which the unit is stuck, and the duration of action required. The amount of active agent and area of the pharmaceutical composition etc. may

TABLE 2

| Time after Treatment | n | AChE activity in % of controls ± SD | | | | | |
|---|---|---|---|---|---|---|---|
| | | Cortex | Hippocampus | Striatum | Pons/Medulla | Heart | Blood |
| Transdermal 30 µmol/kg | | | | | | | |
| 0.5 hours | 6 | 86.1 ± 5.6 | 86.7 ± 5.9 | 89.7 ± 8.4 | 91.5 ± 3.8 | 109.0 ± 9.3 | 71.3 ± 12.3 |
| 6 hours | 6 | 42.4 ± 11.7 | 45.7 ± 15.0 | 65.9 ± 15.5 | 53.6 ± 13.3 | 52.0 ± 13.1 | 41.9 ± 13.1 |
| 24 hours | 6 | 73.8 ± 5.7 | 80.4 ± 8.8 | 81.0 ± 8.2 | 85.3 ± 4.2 | 63.9 ± 12.5 | 78.1 ± 17.8 |
| Oral 10 µmol/kg | | | | | | | |
| 0.5 hours | 6 | 21.0 ± 3.5 | 19.7 ± 3.8 | 32.9 ± 10.7 | 26.6 ± 4.0 | 71.2 ± 11.2 | 34.0 ± 2.0 |
| 6 hours | 6 | 65.3 ± 21.3 | 62.0 ± 15.4 | 87.5 ± 8.8 | 80.3 ± 9.2 | 101.0 ± 7.0 | 77.2 ± 14.7 |
| 24 hours | 6 | 99.2 ± 8.9 | 97.2 ± 7.1 | 96.7 ± 3.3 | 104.1 ± 6.8 | 94.2 ± 9.2 | 97.2 ± 13.8 |
| Subcutaneous 8 µmol/kg | | | | | | | |
| 0.5 hours | 6 | 16.8 ± 2.0 | 18.3 ± 3.1 | 28.2 ± 12.2 | 20.9 ± 2.9 | 33.3 ± 5.6 | 17.4 ± 4.1 |
| 6 hours | 6 | 85.1 ± 1.6 | 81.4 ± 7.6 | 82.9 ± 2.8 | 87.1 ± 4.1 | 51.0 ± 17.9 | 79.5 ± 8.2 |
| 24 hours | 6 | 93.8 ± 5.9 | 99.9 ± 9.9 | 91.0 ± 2.3 | 98.7 ± 6.0 | 65.7 ± 21.2 | 105.7 ± 16.8 |

Control values (pmole/mg × min. ± SD n = 15):
Cortex: 3.67 ± 0.30
Hippocampus: 4.42 ± 0.30
Striatum: 33.8 ± 3.08
Pons/Medulla: 7.98 ± 0.36
Heart: 2.27 ± 0.39
Blood: 311.4 ± 44.2

Thus in another aspect the present invention provides a pharmaceutical composition for systemic transdermal administration incorporating as an active agent a compound of formula I' in free base or pharmaceutically acceptable acid addition salt form.

In a further aspect the present invention provides a method of systemically administering an active agent of formula I' in free base or pharmaceutically acceptable acid addition salt form which comprises administering the active agent to the skin.

The active agents may be administered in any conventional liquid or solid transdermal pharmaceutical composition, e.g. as described in Remington's Pharmaceutical Sciences 16th Edition Mack; Sucker, Fuchs and Spieser, Pharmazeutische Technologie 1st Edition, Springer and in GB 2098865 A or DOS 3212053 the contents of which are incorporated herein by reference.

Conveniently the composition is in the form of a viscous liquid, ointment or solid reservoir or matrix. For example the active agent is dispersed throughout a solid reservoir or matrix made of a gel or a solid polymer, e.g. a hydrophilic polymer as described in European Patent Application No. 155,229.

The active agent may be incorporated in a plaster.

The compositions for transdermal administration may contain from about 1 to about 20% by weight of active agent of formula I' in free base or pharmaceutically acceptable acid addition salt form.

The pharmaceutical compositions for transdermal administration may be used for the same indications as for oral or intravenous administration. The amount of pharmaceutically active agent to be administered will individually depend on be determined by routine bioavailability tests comparing the blood levels of active agents after administration of the active agent in a pharmaceutical composition according to the invention to intact skin and blood levels of active agent observed after oral or intravenous administration of a therapeutically effective dose of the pharmacologically active agent.

Given the daily dose of a drug for oral administration, the choice of a suitable quantity of drug to be incorporated in a transdermal composition according to the invention will depend upon the pharmacokinetic properties of the active agent, including the first pass effect; the amount of drug which can be absorbed through the skin from the matrix in question for a given area of application and in a given time; and the time for which the composition is to be applied. Thus, a drug with a high first pass effect may require a relatively low quantity in the transdermal composition when compared with the oral daily dose, since the first pass effect will be avoided. On the other hand, generally a maximum of only approximately 50% of the drug in the matrix is released through the skin in a 3 day period.

The pharmaceutical compositions of the invention in general have for example an effective contact area of drug reservoir on the skin of from about 1 to about 50 square centimeters, preferably about 2 to 20 square centimeters, and are intended to be applied for from 1–7 days, preferably 1–3 days.

Compound A may for example be administered at a dose of 10 mg in a patch of ca. 10 cm², once every three days.

The following example illustrates the invention.

EXAMPLE 2

Preparation of a Transdermal Composition
Containing a Hydrophilic Polymer

| Composition | |
|---|---|
| Compound of formula I', e.g. compound A | 20% |
| Hydrophilic polymer, e.g. Eudragit E 100* | 30% |
| Non swellable acrylate polymer, e.g. Durotack 280–2416** | 44% |
| Plasticizer, e.g. Brij 97*** | 6% |

*Registered Trade Mark, available from Röhm, Darmstadt, W. Germany
**Registered Trade Mark, available from Delft National Chemie Zutphen, Netherlands
***Registered Trade Mark, available from Atlas Chemie, W. Germany The components are added to acetone or ethanol or another appropriate volatile organic solvent and mixed to give a viscous mass. The mass is spread on top of an aluminised polyester foil (thickness 23 microns) using a conventional apparatus, to produce a film of thickness 0.2 mm when wet. The film is allowed to dry at room temperature over 4 to 6 hours. The aluminium foil is then cut up into patches about 10 sq cm in area.

What we claim is:

1. The (S)-[N-ethyl-3-[(1-dimethylamino)ethyl]-N-methyl-phenyl-carbamate] enantiomer of formula I substantially free of its (R) isomer

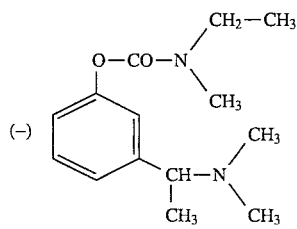

in free base or acid addition form.

2. The compound of claim 1 which is the hydrogen tartrate salt of (S)-N-ethyl-3-[(1-dimethylamino)ethyl]-N-methyl-phenylcarbamate.

3. A pharmaceutical composition which comprises a compound of claim 1 in free base or pharmaceutically acceptable acid addition salt form, in association with a pharmaceutical carrier or diluent.

4. A method of treating senile dementia, which comprises administering a therapeutically effective amount of a compound of claim 1 in free base or pharmacologically acceptable acid addition salt form to a subject in need of such treatment.

5. A method of treating Alzheimer's disease, which comprises administering a therapeutically effective amount of a compound of claim 1 in free base or pharmacologically acceptable acid addition salt form to a subject in need of such treatment.

6. A method of treating Huntington's chorea, tardive dyskinesias, hyperkinesia, mania, acute confusion disorders, Down's syndrome or Friedrich's ataxia, which comprises administering a therapeutically effective amount of a compound of claim 1 in free base or pharmaceutically acceptable acid addition salt form to a subject in need of such treatment.

7. A method of systemically administering a compound of claim 1 in free base or pharmaceutically acceptable acid addition salt form, which comprises administering the active agent transdermally through the skin.

8. A systemic transdermal pharmaceutical composition according to claim 3 comprising a therapeutically effective amount of (S)-N-ethyl-3-[(1-dimethyl-amino)ethyl]-N-methyl-phenyl-carbamate in free base or pharmaceutically acceptable acid addition salt form, and a pharmaceutically acceptable carrier therefor suitable for systemic transdermal administration.

9. A systemic transdermal pharmaceutical composition according to claim 3 comprising a therapeutically effective amount of the hydrogen tartrate salt of (S)-N-ethyl-3-[(1-dimethyl-amino)ethyl]-N-methyl-phenyl-carbamate, and a pharmaceutically acceptable carrier therefor suitable for systemic transdermal administration.

10. A systemic transdermal pharmaceutical composition according to claim 8 in which the (S)-N-ethyl-3-[(1-dimethyl-amino)ethyl]-N-methyl-phenyl-carbamate is in free base form.

11. A systemic transdermal pharmaceutical composition according to claim 8 in which the pharmaceutically acceptable carrier is a transdermal patch.

12. A method according to claim 7 in which the compound is in free base form.

* * * * *